(12) United States Patent
Strommer et al.

(10) Patent No.: US 9,717,468 B2
(45) Date of Patent: Aug. 1, 2017

(54) SYSTEM AND METHOD FOR POSITIONING AN ARTIFICIAL HEART VALVE AT THE POSITION OF A MALFUNCTIONING VALVE OF A HEART THROUGH A PERCUTANEOUS ROUTE

(75) Inventors: Gera Strommer, Haifa (IL); Uzi Eichler, Haifa (IL); Liat Schwartz, Haifa (IL); Itzhak Shmarak, Nofit (IL)

(73) Assignee: MediGuide Ltd., Haifa (IL)

( * ) Notice: Subject to any disclaimer, the term of this patent is extended or adjusted under 35 U.S.C. 154(b) by 2351 days.

(21) Appl. No.: 11/329,824

(22) Filed: Jan. 10, 2006

(65) Prior Publication Data

US 2007/0173861 A1 Jul. 26, 2007

(51) Int. Cl.
*A61B 6/12* (2006.01)
*A61B 5/06* (2006.01)
*A61B 6/00* (2006.01)
*A61F 2/24* (2006.01)
*A61B 5/055* (2006.01)
*A61B 5/00* (2006.01)
*A61B 8/08* (2006.01)
*A61B 34/20* (2016.01)

(52) U.S. Cl.
CPC .................. *A61B 6/12* (2013.01); *A61B 5/06* (2013.01); *A61B 6/465* (2013.01); *A61B 6/481* (2013.01); *A61B 6/504* (2013.01); *A61B 6/5235* (2013.01); *A61B 8/0841* (2013.01); *A61B 8/5238* (2013.01); *A61F 2/2427* (2013.01); *A61B 5/055* (2013.01); *A61B 5/7289* (2013.01); *A61B 6/503* (2013.01); *A61B 6/541* (2013.01); *A61B 8/0833* (2013.01); *A61B 2034/2051* (2016.02)

(58) Field of Classification Search
CPC .. A61B 6/12; A61B 6/46; A61B 6/465; A61B 5/06; A61B 6/541; A61F 2/2427
USPC ......................................... 623/1.21; 600/424
See application file for complete search history.

(56) References Cited

U.S. PATENT DOCUMENTS

| | | | | |
|---|---|---|---|---|
| 5,928,248 | A * | 7/1999 | Acker | 623/1.11 |
| 5,957,949 | A | 9/1999 | Leonhardt et al. | |
| 6,246,898 | B1 * | 6/2001 | Vesely et al. | 600/424 |
| 6,402,780 | B2 | 6/2002 | Williamson, IV et al. | 623/2.11 |
| 6,651,671 | B1 | 11/2003 | Donlon et al. | 128/898 |
| 6,821,297 | B2 | 11/2004 | Snyders | 623/2.18 |
| 6,830,585 | B1 | 12/2004 | Artof et al. | 623/2.11 |
| 6,899,704 | B2 | 5/2005 | Sterman et al. | 606/1 |

(Continued)

FOREIGN PATENT DOCUMENTS

WO WO2005/077293 A2 8/2005

*Primary Examiner* — Thomas J Sweet
*Assistant Examiner* — Seema Mathew
(74) *Attorney, Agent, or Firm* — Dykema Gossett PLLC

(57) ABSTRACT

Method for positioning an artificial heart valve at the anatomic position of a malfunctioning heart valve of a heart of a patient, by employing a catheter bearing the artificial heart valve and a valve fixation device, at the tip of the catheter, the method including the procedures of receiving a marking input associated with an image of the heart, and respective of the anatomic position, in a medical positioning system (MPS) coordinate system, moving the tip toward the anatomic position, constantly detecting the current position of the artificial heart valve, and producing an indication when the current position substantially matches the anatomic position, thereby enabling the catheter to fix the malfunctioning heart valve in place, by the valve fixation device.

11 Claims, 10 Drawing Sheets

(56) References Cited

U.S. PATENT DOCUMENTS

| | | | |
|---|---|---|---|
| 7,195,641 B2* | 3/2007 | Palmaz et al. | 623/2.18 |
| 2002/0049375 A1* | 4/2002 | Strommer et al. | 600/407 |
| 2003/0051733 A1 | 3/2003 | Kotmel et al. | |
| 2004/0019447 A1* | 1/2004 | Shachar | 702/115 |
| 2004/0073301 A1 | 4/2004 | Donlon et al. | |
| 2004/0097804 A1* | 5/2004 | Sobe | 600/424 |
| 2004/0138548 A1* | 7/2004 | Strommer | A61B 5/0555 600/407 |
| 2005/0107688 A1 | 5/2005 | Strommer | |
| 2007/0276216 A1* | 11/2007 | Beyar | A61B 6/12 600/407 |
| 2008/0183071 A1* | 7/2008 | Strommer | A61B 5/06 600/424 |
| 2008/0221439 A1* | 9/2008 | Iddan | A61B 6/5217 600/424 |
| 2010/0210938 A1* | 8/2010 | Verard et al. | 600/424 |
| 2011/0087110 A1* | 4/2011 | Nathan | A61B 5/053 600/476 |
| 2011/0230758 A1* | 9/2011 | Eichler | A61B 5/06 600/424 |
| 2013/0172730 A1* | 7/2013 | Cohen | A61B 6/12 600/424 |
| 2014/0270436 A1* | 9/2014 | Dascal | G06T 7/11 382/130 |
| 2015/0297151 A1* | 10/2015 | Florent | A61B 90/10 600/424 |

* cited by examiner

SYSTEM AND METHOD FOR POSITIONING AN ARTIFICIAL HEART VALVE AT THE POSITION OF A MALFUNCTIONING VALVE OF A HEART THROUGH A PERCUTANEOUS ROUTE

FIELD OF THE DISCLOSED TECHNIQUE

The disclosed technique relates to percutaneous cardiac operations in general, and to methods and systems for replacing a malfunctioning heart valve, in particular.

BACKGROUND OF THE DISCLOSED TECHNIQUE

The heart of a mammal such as a human being, rodent, swine, cow, and the like, includes four valves (i.e., mitral valve, aortic valve, pulmonary valve, and tricuspid valve). The mitral valve controls the blood flow between the left atrium and the left ventricle. The tricuspid valve controls the blood flow between the right atrium and the right ventricle. The aortic valve controls the blood flow from the left ventricle to the vascular system of the body. The pulmonary valve controls the blood flow from the right ventricle to the lungs. Defective operation of any of these four valves brings about a specific medical complication. For example, a defective mitral valve may cause regurgitation (i.e., leakage between the left ventricle and the left atrium), thereby reducing the pumping efficiency of the heart, and depriving major organs of the body from oxygen and the necessary substances.

Replacement of a heart valve is a common practice in medicine. The heart valve, in this operation, is replaced by an artificial valve. An artificial valve can be either a mechanical valve or a tissue valve. A mechanical valve can be either a ball type valve or a disk type valve. Examples of the ball type valve include the Starr-Edwards valve, Magovern-Cromie Sutureless valve, and Smeloff-Sutter valve. A disk valve can be either a single leaflet disk valve (e.g., Bjork-Shiley valve, Medtronic-Hall valve, Omniscience valve), or a bi-leaflet disk valve (e.g., St. Jude valve, Carbomedics valve, Edwards-Duromedics valve).

A tissue valve can be either an animal tissue valve (i.e., xenograft or heterograft), or a human tissue valve (i.e., homograft or autograft]). A xenograft can be of valve tissue, typically porcine (i.e., pig valve tissue). Alternatively, a xenograft can be of non-valve tissue, for example bovine (i.e., cow pericardium). A homograft valve is a valve transplant from another person. An autograft is a valve moved from one position to another within the same patient, or a valve self-transplant.

Such valve replacement procedures are usually performed in an open-heart setting (i.e., cutting the sternum and opening up the rib cage, in order to gain direct access to the heart and the respective valve). As the surgeons gained more experience in this type of operation, the success rate of the surgery increased and many patients benefited from longer and relatively disease-free life.

However, due to the massive incisions that are performed in an open-heart surgery, the patient undergoes a substantially long and painful recovery period accompanied by a long term post-operation pain and morbidity. Furthermore, the patient has to follow a strict regimen following the surgery, in order to reduce future medical complications, for example due to accompanied infections.

Heart valve replacement surgery may also be performed in a closed-chest setting, by gaining access to the heart valve, either by performing a number of access holes in the chest (i.e., minimally invasive surgery), or by entering the heart chambers through the vascular system (e.g., through the right subclavian vein, or the inferior vena cava—i.e., by performing a percutaneous operation). One benefit of closed-chest surgery, is that the accompanied medical complications are much less than those of the open-heart surgery, and the patient can return to normal activity shortly following the surgery. Hence, high-risk patients, mostly morbid elderly, can benefit from percutaneous heart valve replacement surgery.

However, in a percutaneous operation, when a catheter is used, the surgeon faces the difficulty of determining the precise location of the malfunctioning heart valve, because the leaflet tissue of the malfunctioning heart valve has similar biological properties as the rest of the heart tissue. Therefore, the malfunctioning heart valve can not be clearly differentiated from the background, in an image of the heart (e.g., X-ray, computer tomography, or magnetic resonance imaging), unless the malfunctioning heart valve is calcified. A prevalent method in detecting the location of the valve, is injecting a contrast agent in the vascular system. Then a first image is acquired when the left ventricle, for example, is filled with the contrast agent, and a second image is acquired when the left atrium is filled with the contrast agent.

Since the malfunctioning valve is generally calcified, the location thereof is indicated accordingly, in each of the first and the second images. The medical staff member alternates between the first image and the second image, to estimate the approximate location of the malfunctioning heart valve. The surgeon maneuvers the artificial heart valve toward the approximate location of the malfunctioning heart valve, based on his or her visual memory.

The catheter which is used in this operation is a balloon catheter, which includes an inflatable balloon at the tip thereof. The artificial heart valve, an outer nitinol stent, and an inner platinum stent are secured to the inflatable balloon. The inner platinum stent contains the artificial heart valve. The outer nitinol stent and the inner platinum stent are secured together, along the commissures of the artificial heart valve, instead of the leaflets of the artificial heart valve. The surgeon aligns the sections of the expanded outer nitinol stent with the leaflets of the malfunctioning heart valve, by presuming that the tip of the catheter (i.e., the artificial heart valve) is located at the location of the malfunctioning heart valve, and then she inflates the inflatable balloon.

When the inflatable balloon is inflated, the sections along the leaflets of the artificial heart valve expand, while leaving the sections along the commissures, secured to the inner platinum stent. The inner platinum stent is expanded, thereby deploying the outer nitinol stent in the position of the malfunctioning heart valve. In this manner, the leaflets of the malfunctioning heart valve are sandwiched between the outer nitinol stent and inner platinum stent, and the leaflets of the malfunctioning heart valve are fixed against the side wall of the coronary ostia (i.e., the heart chamber opening). The surgeon then deflates the inflatable balloon, thereby permanently fixing in place the outer nitinol stent, the inner platinum stent, and the artificial heart valve. The medical staff member then removes the catheter from the body of the patient.

In order to fix the artificial heart valve in place, the surgeon has to arrest heart function for a very short period of time. Otherwise, if the inflatable balloon is inflated or maneuvered within the chambers of the heart, while the myocardium of the heart is continuously contracting, then the inflatable balloon will likely be sucked into the chamber. This event can severely injure the heart tissues or block the blood flow within the heart (i.e., cause ischemic heart failure). The heart function can be arrested for only a very short time (i.e., tens of seconds), otherwise, the brain and other organs of the body are deprived of oxygen, which may result in permanent damage. Therefore, it is clear that the surgeon is given a very short time, to perform the actual task of fixing in place the artificial heart valve. Alternatively, the medical staff member can employ an elongated tubular manipulator having an ejector, to eject the artificial heart valve at the location of the malfunctioning heart valve.

U.S. Pat. No. 6,899,704 B2 issued to Sterman et al., and entitled "Devices and Methods for Intracardiac Procedures", is directed to a less-invasive surgical procedure within the heart and great vessels of the thoracic cavity. One such surgical procedure is closed-chest mitral valve replacement. A percutaneous intercostal penetration is performed in the chest of the patient (i.e., an incision through the chest wall between two adjacent ribs, in which the rib cage and sternum of the patient remain substantially intact). An endoscope is inserted though the intercostal penetration (e.g., through an access cannula or a trocar sleeve). The endoscope is manipulated to view the right side of the heart.

A video camera is mounted to the endoscope and connected with a video monitor, which provides a video image of the interior of the thoracic cavity. The patient is placed on cardiopulmonary bypass, the right lung is partially collapsed and cardiac function is arrested. Venting may be performed to maintain decompression of the left side of the heart. A surgical cutting instrument (e.g., angled scissors) and a grasping instrument (e.g., forceps) are inserted though the intercostal penetration, and used to cut through the right side of the left atrium to form an atriotomy.

A retractor is used to retract the wall of the left atrium on the anterior side of the atriotomy, exposing the mitral valve within the left atrium. A clamping device maintains the retractor in position. The mitral valve leaflets are removed using the surgical cutting instrument. The valve annulus is sized for selecting a replacement valve of the proper size. The replacement valve is mounted to an introducer. The introducer is advanced through the atriotomy, until the replacement valve is positioned against or within the valve annulus. The replacement valve may be attached to the heart, by suturing to the valve annulus. The atriotomy is then closed, all instruments are removed from the thoracic cavity, and all incisions and penetrations are closed. The lung is re-inflated, cardiac function restarted, and cardiopulmonary bypass discontinued.

U.S. Pat. No. 6,821,297 B2 issued to Snyders, and entitled "Artificial Heart Valve, Implantation Instrument and Method Therefor", is directed to an artificial valve for repairing a damaged heart valve. The artificial valve includes a flexibly resilient external frame and a flexible valve element attached to the center of the frame. The frame includes a plurality of stenting elements, extending between opposite ends of the frame, a band extending around the frame between the stenting elements, and anchors, at each end of the stenting elements. The stenting elements and the band enable the frame to be compressed to a collapsed configuration. For repairing a damaged mitral valve, an endothoracoscopic instrument is inserted through a jugular or femoral vein.

The endothoracoscopic instrument includes a tubular holder, and a tubular manipulator attached to the holder, for manipulating the holder into position. An ejector is positioned in a hollow interior of the holder, for ejecting the artificial valve from the holder. The artificial valve frame is placed in the collapsed configuration inside the holder. A small opening is made in the chest wall of the patient, and a small incision is made in the heart. The holder end of the instrument is inserted through the opening and the incision.

The artificial valve is ejected into a position between the cusps (i.e., which separate the left atrium from the left ventricle) of the damaged mitral valve. The anchors (e.g., hooks) attach the frame of the artificial valve into position between the cusps. The instrument is withdrawn from the chest, and the opening and incision are closed. The flexible valve element opens when the fluid pressure in the left atrium is greater than the fluid pressure in the left ventricle, permitting downstream flow between the left atrium and the left ventricle. The flexible valve element closes when the fluid pressure in the left ventricle is greater than the fluid pressure in the left atrium, blocking flow reversal from the left ventricle to the left atrium.

U.S. Pat. No. 6,830,585 B1 issued to Artof et al., and entitled "Percutaneously Deliverable Heart Valve and Methods of Implantation", is directed to a stentless prosthetic heart valve suitable for replacement of a defect or diseased human heart valve, and methods of implantation. The prosthetic valve has three leaflets secured together by sutures. Each of the leaflets has an in-flow edge, an out-flow edge, and side edges. The leaflets are secured together by sutures, forming an annulus at the in-flow edge and the commissure tissue. A plurality of tabs are mounted to the commissure tissue of the leaflets (i.e., the tissue at the commissural end point of any two leaflets). The annulus is connected to an annulus base support, which is collapsible and expandable.

The annulus base support is covered with a cloth cover, for attaching the annulus base support onto the heart tissue. During implantation, the prosthetic valve is collapsed and positioned within a delivery means (e.g., a catheter). The delivery means is introduced into the aorta area of the patient, through a percutaneous intercostal penetration of the chest or an opening of a blood vessel.

The valve is deployed from the delivery means and expanded, with the annulus base support positioned at the location of the anatomical heart valve. The distal end of the commissure tissues are secured to the aorta wall using a valve rivet. The valve rivet is inserted endoluminally to the prosthetic valve position. The rivet tip penetrates through the commissure tissue and the aorta wall. The valve rivet is pushed forward, which releases preformed wires which expand radially outwards to hold the aorta wall in place. The valve rivet is then pulled back, compressing and expanding the preformed wires, thereby securing the commissure tissue to the aorta wall.

U.S. Pat. No. 6,651,671 B1 issued to Donlon et al., and entitled "Less-Invasive Devices and Methods for Cardiac Valve Surgery", is directed to surgical instruments for a less-invasive heart surgery, such as the repair and replacement of heart valves. One such surgery type is aortic valve replacement. The patient is placed under general anesthesia, cardiopulmonary bypass is established to support circulation, and cardioplegic arrest is induced. At least one access port is formed percutaneously in the intercostal spaces between the ribs on the right anterior side of the chest. The access port may include a trocar sleeves, or an incision in which tissue is retracted apart to create a small opening.

The pericardium is opened to expose the ascending aorta, and an incision is formed in the ascending aorta wall (i.e., an aortotomy), using thoracoscopic angled scissors. The aortotomy is retracted open (e.g., using sutures), exposing the aortic valve. The leaflets of the aortic valve are removed using the angled scissors and forceps, positioned through the access ports. Thoracoscopic rongeurs remove any calcific deposits and any remaining leaflet tissues around the inner surface of the valve annulus.

The valve annulus is sized using a valve sizing device, to determine the appropriate size for the replacement valve. The prosthetic valve (e.g., a mechanical valve) is mounted to a holder on a delivery handle. The delivery handle is advanced into the chest through an inner lumen of an access port. The prosthetic valve is positioned adjacent to the valve annulus, and released from the delivery handle. The prosthetic valve is secured to the valve annulus, such as by using sutures. The moveable leaflets of the prosthetic valve may be tested for proper functioning using a probe. The aortotomy is closed, cardiac function is resumed, cardiopulmonary bypass is disabled, all incisions are closed, and all instruments are removed from the patient.

U.S. Pat. No. 6,402,780 B2 issued to Williamson, I V et al., and entitled "Means and Method of Replacing a Heart Valve in a Minimally Invasive Manner", is directed to a device and method of fastening an aortic valve prosthesis into living tissue. A flexible and sutureless sewing cuff is attached to the aortic annulus using a fastener delivery tool. The fastener delivery tool includes an operating handle and a fastener deployment knob on one end, and an operating head on the other end. The operating head includes a housing containing fasteners (e.g., staples).

The cuff is stretched over the operating head. The fastener delivery tool is inserted into the patient via an incision located in the thorax. The fastener delivery tool positions the cuff adjacent to the aortic annulus tissue, and holds the cuff securely against the tissue throughout the fastener setting procedure. The tool drives a fastener through the cuff and the tissue, and then folds over the fastener legs, thereby securely attaching the cuff to the tissue. A series of fasteners are likewise arranged throughout the entire circumference of the cuff (e.g., spaced in a staggered and uniform pattern).

The fastener delivery tool is removed from the heart, and the valve prosthesis is inserted into the aortic lumen and positioned inside the cuff. The valve prosthesis is attached to the cuff using drawstrings, which extend outside the body of the patient. Indicating means (e.g., a garter spring) located in the lower section of the cuff, holds the valve in place, and provides a signal to the surgeon when the valve body is properly seated in the cuff before activating the drawstrings. The indicating means later provides a tactile signal to the surgeon indicating that the valve is securely attached to the cuff.

US Patent Publication No. 20020049375 entitled "Method and Apparatus for Real Time Quantitative Three-Dimensional Image Reconstruction of a Moving Organ and Intra-Body Navigation", is directed to a system for displaying an image of a lumen of a patient into which a surgical catheter is inserted, while taking into account the movements of the lumen caused by the heart beats of the patient. The system includes the surgical catheter, an imaging catheter, an imaging system, a medical positioning system (MPS), a transmitter, a body MPS sensor, a processor, a plurality of electrocardiogram (ECG) electrodes, an ECG monitor, a database, and a display. The surgical catheter includes a catheter MPS sensor located at a tip thereof. The imaging catheter includes an imaging MPS sensor and an image detector, both located at a tip of the imaging catheter.

The ECG electrodes are attached to the body of the patient and to the ECG monitor. The body MPS sensor is attached to the body of the patient and to the MPS. The processor is coupled with the imaging system, the MPS, the ECG monitor, the database and with the display. The MPS is coupled with the transmitter. During the scanning procedure the MPS is coupled with the imaging MPS sensor. During the surgical procedure the MPS is coupled with the catheter MPS sensor. The imaging system is coupled with the image detector. The imaging MPS sensor and the catheter MPS sensor send a signal respective of the position and orientation of the tip of the imaging catheter and the surgical catheter, respectively, to the MPS.

During the scanning procedure, an operator inserts the imaging catheter into the lumen and advances it therein, while the image detector scans the inner wall of the lumen and transmits detected two-dimensional images to the imaging system. The processor reconstructs a plurality of three-dimensional images according to the two-dimensional images and according to the coordinates of the tip of the imaging catheter determined by the MPS, while the processor associates each three-dimensional image with a respective activity state of the heart of the patient.

During the surgical procedure, the operator inserts the surgical catheter into the lumen and the catheter MPS sensor sends a location signal respective of the position and orientation of the tip of the surgical catheter to the MPS. As the operator moves the surgical catheter within the lumen, the processor determines a sequence of three-dimensional images of the lumen by retrieving data from the database, and according to the current position and orientation of the tip of the surgical catheter and the current activity state of the heart of the patient. The display displays the three-dimensional images in sequence, according to a video signal received from the processor.

SUMMARY OF THE DISCLOSED TECHNIQUE

It is an object of the disclosed technique to provide a novel method and system for replacing a malfunctioning heart valve of the heart of a patient. In accordance with the disclosed technique, there is thus provided a method for positioning an artificial heart valve at the anatomic position of a malfunctioning heart valve of a heart of a patient, by employing a catheter bearing the artificial heart valve and a valve fixation device, at the tip of the catheter.

The method includes the procedures of receiving a marking input associated with an image of the heart, and respective of the anatomic position, in a medical positioning system (MPS) coordinate system, moving the tip toward the anatomic position, constantly detecting the current position of the artificial heart valve, and producing an indication when the current position substantially matches the anatomic position, thereby enabling the catheter to fix the malfunctioning heart valve in place, by the valve fixation device.

In accordance with another aspect of the disclosed technique, there is thus provided a system for positioning an artificial heart valve at the anatomic position of a malfunctioning heart valve of a heart of a patient. The system includes a catheter bearing the artificial heart valve and a valve fixation device, at the tip of the catheter, a medical positioning system (MPS) sensor located at the tip of the catheter, an MPS coupled with the MPS sensor, and a processor coupled with the MPS. The catheter is employed for fixing in place the artificial heart valve, at the anatomic position, by the valve fixation device.

The processor determines the anatomic position, according to a respective marking input received from a user interface coupled with the processor. The processor constantly determines the current position, while the catheter is moving toward the anatomic position. The processor produces an indication via the user interface, when the processor determines that the current position substantially matches the anatomic position.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by enabling the medical staff member to mark the anatomic position of a malfunctioning heart valve of the heart of a patient, on an image of the heart, in a three-dimensional coordinate system of a medical positioning system (MPS). The medical staff member moves a valve replacement catheter bearing an artificial heart valve and a valve fixation device at the tip thereof, toward the anatomic position. The MPS determines when the artificial heart valve has reached the anatomic position, and produces an indication for the medical staff member, accordingly. When the medical staff member receives this indication, she activates the valve fixation device, thereby fixing in place the artificial valve at the location of the malfunctioning heart valve. The medical staff member, then inactivates the valve fixation device and removes the valve replacement catheter from the body of the patient. The valve replacement catheter can be moved within the vascular system, either manually, automatically, or semi-automatically.

The term "position" herein below, refers either to the location, to the orientation or both the location and the orientation, of an object in a three-dimensional coordinate system. The term "artificial heart valve" herein below, refers to a manmade heart valve (e.g., made of a polymer), as well as a tissue valve (e.g., xenograft, heterograft, homograft, autograft, and the like). The term "cardiac arrest" herein below, refers to a state of the heart, in which the heart does not function as a pump, ceasing normal circulation of the blood. Cardiac arrest arises due to the failure of the ventricles of the heart to contract effectively during systole. The term "anatomic position" herein below, refers to the position of a heart valve which has to undergo a heart valve replacement operation.

Figure 1A:
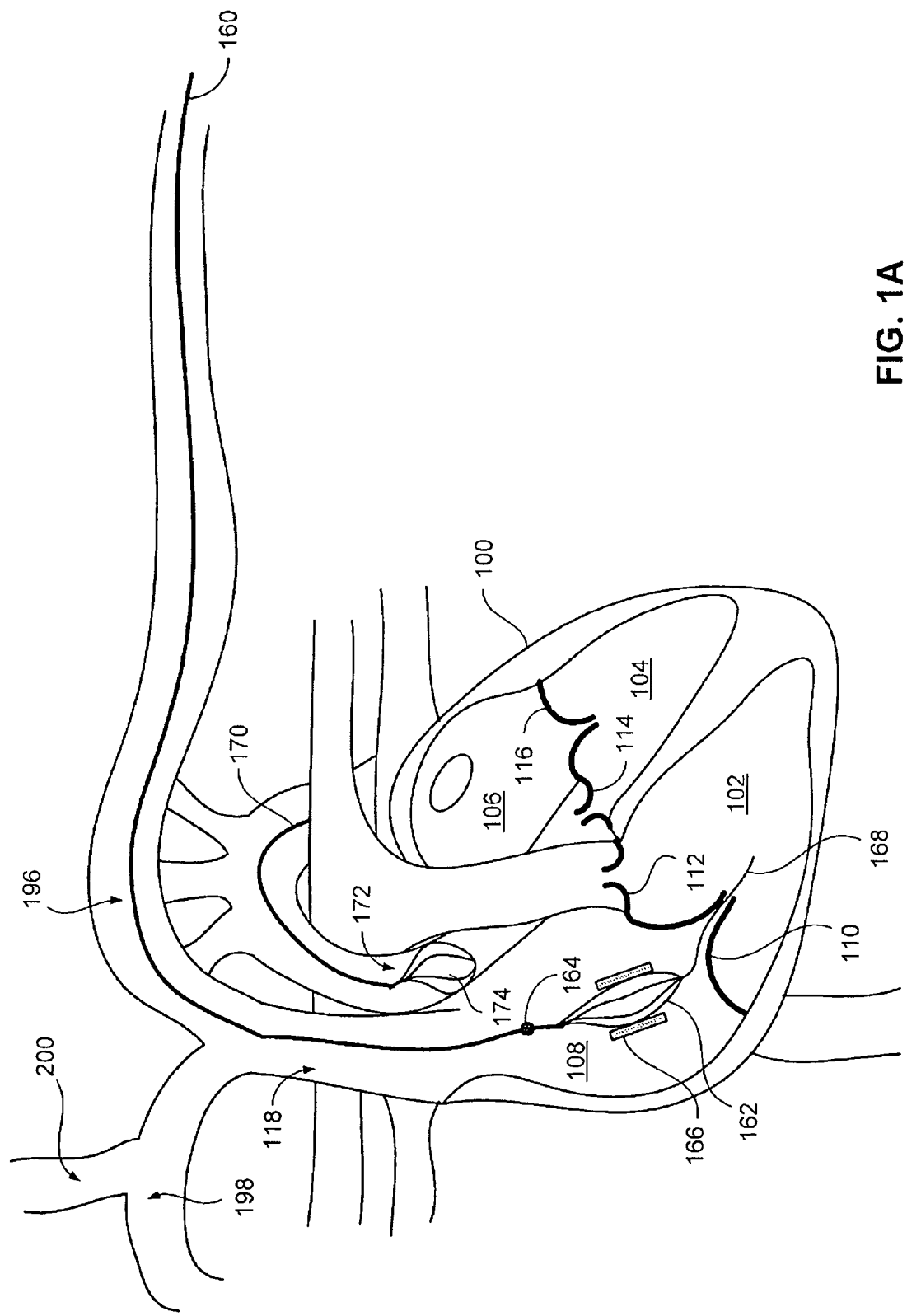
FIG. 1A is a schematic illustration of a heart of a patient who is undergoing a percutaneous cardiac valve replacement operation.
Figure 1B:
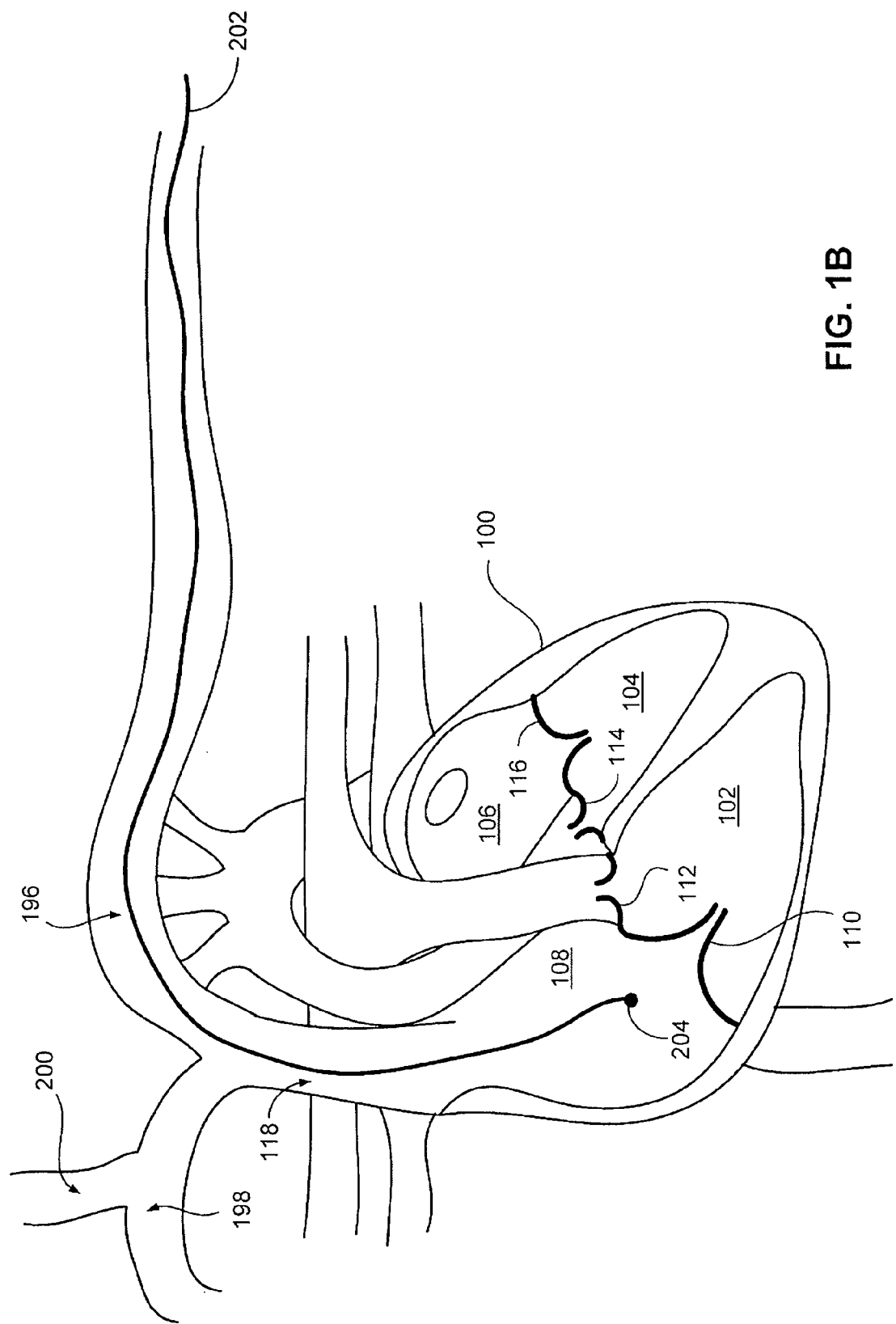
FIG. 1B is a schematic illustration of a mapping catheter located inside a vascular system of the body of the patient of FIG. 1A, for determining the trajectory which a valve replacement catheter has to follow, from a point of insertion into the vascular system to the malfunctioning valve of the heart, according to an embodiment of the disclosed technique.
Figure 1C:
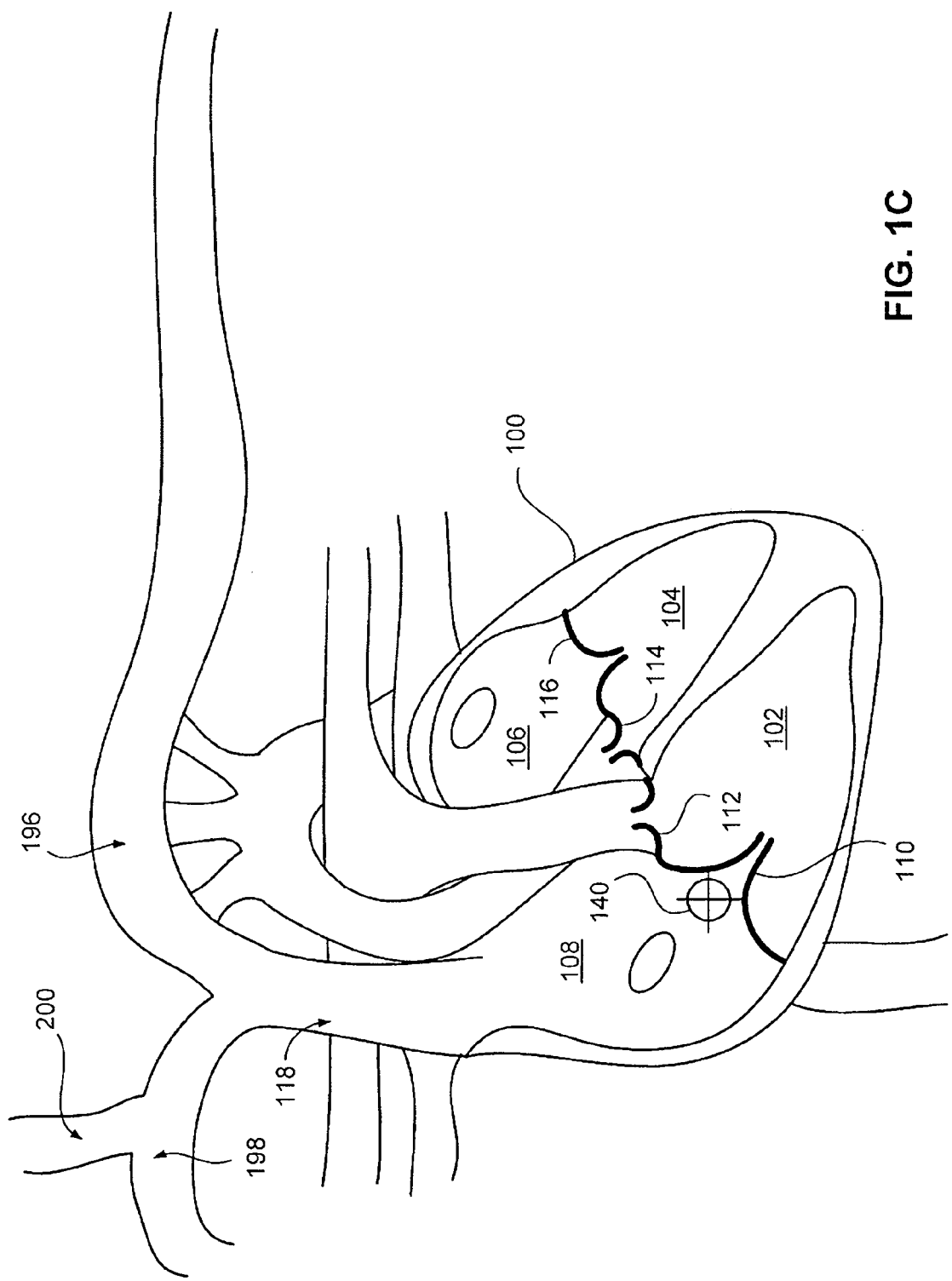
FIG. 1C is a schematic illustration of an image of the heart of FIG. 1A, illustrating an anatomic position of a malfunctioning heart valve of the heart, marked by a medical staff member on an image of the heart, in accordance with another embodiment of the disclosed technique.
Figure 1D:
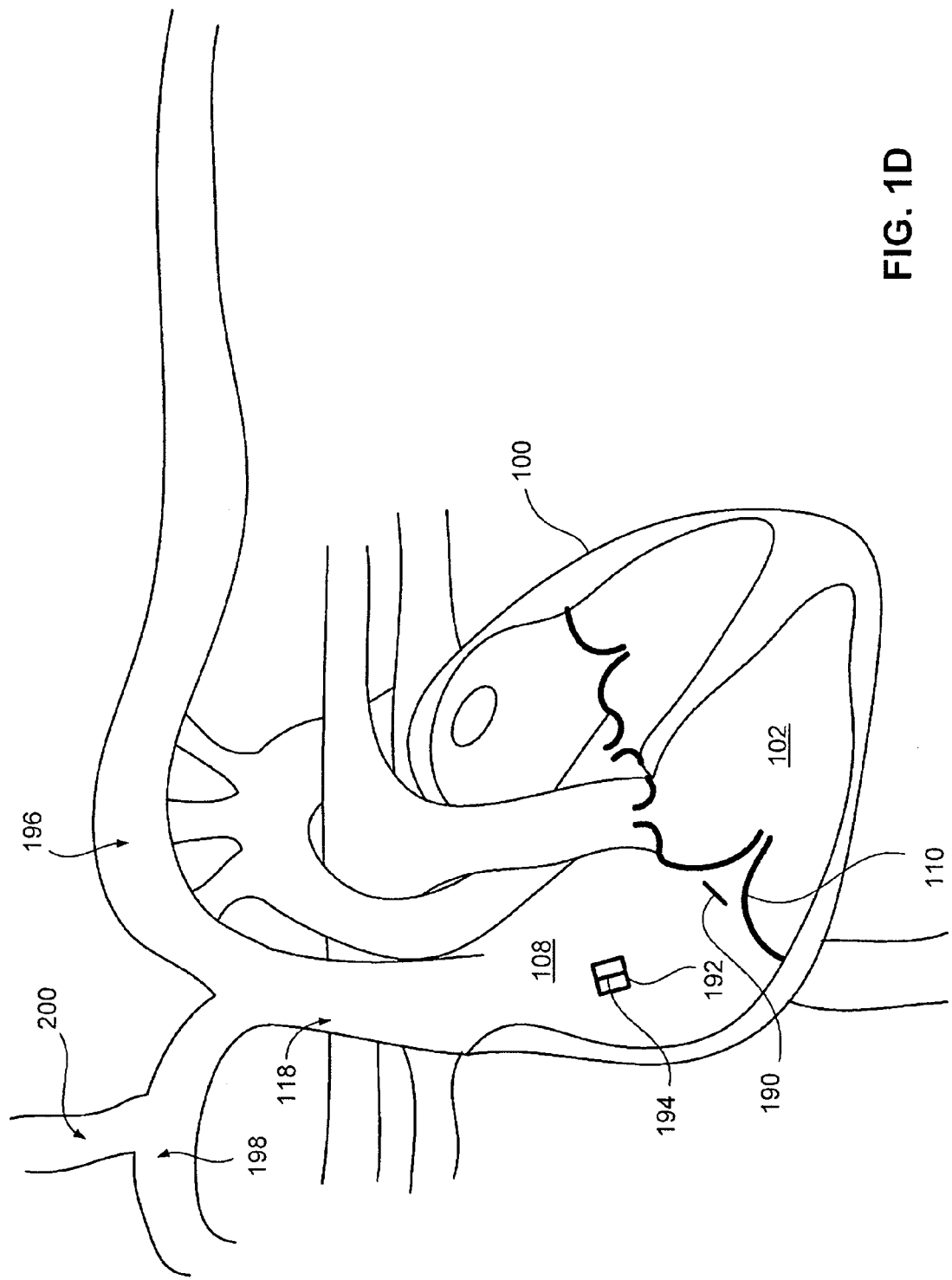
FIG. 1D is a schematic illustration of an anatomic position representation of the malfunctioning heart valve of the heart of FIG. 1A, and the current position representation of an artificial heart valve.
Figure 1E:
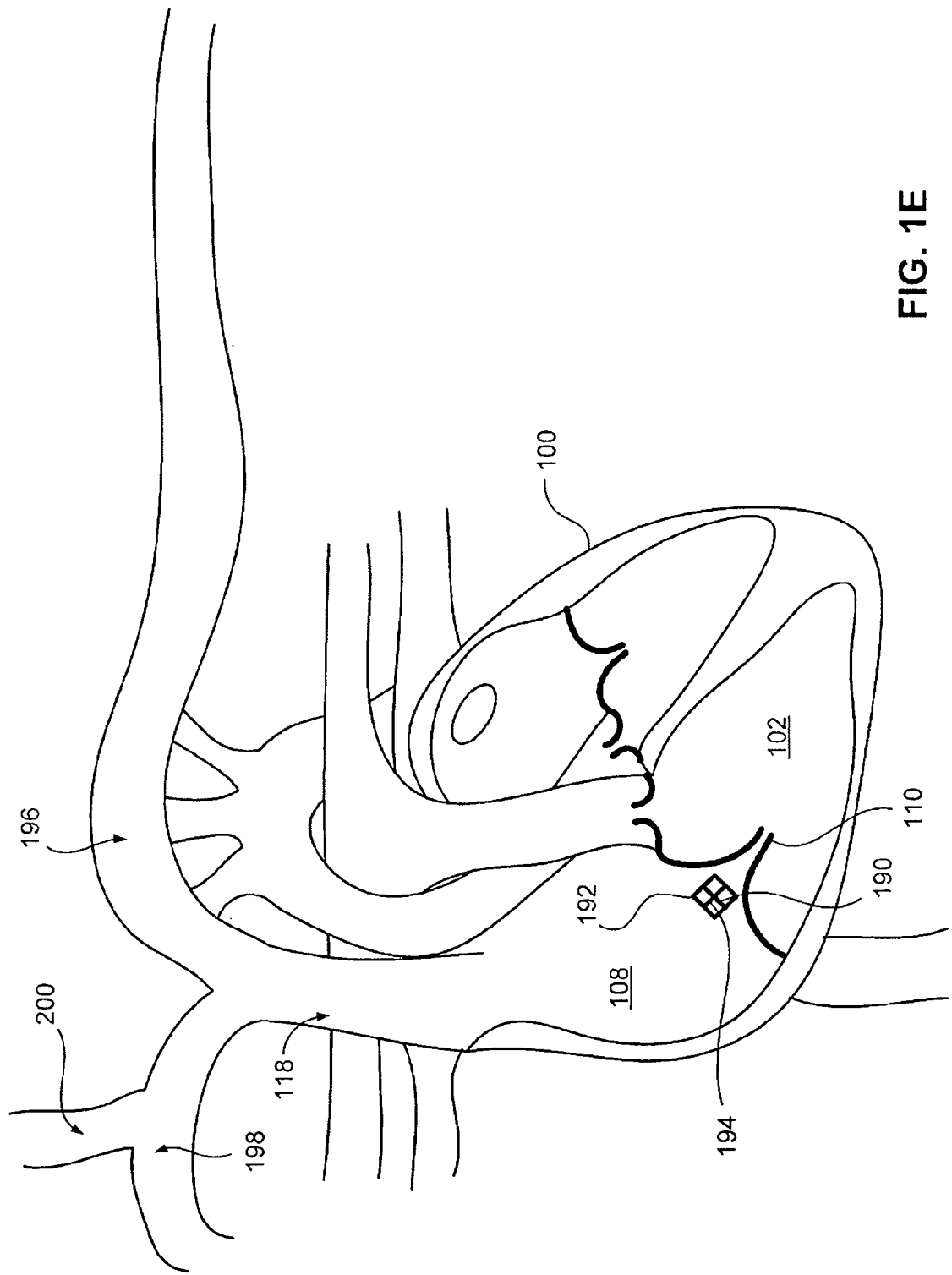
FIG. 1E is a schematic illustration of the anatomic position representation of the malfunctioning heart valve of the heart of FIG. 1A, and the current position representation of the artificial heart valve of FIG. 1D, when the current position of the artificial heart valve is substantially at the anatomic position of the malfunctioning heart.

Reference is now made to FIGS. 1A, 1B, 1C, 1D, and 1E. FIG. 1A is a schematic illustration of a heart generally referenced 100, of a patient who is undergoing a percutaneous cardiac valve replacement operation. FIG. 1B is a schematic illustration of a mapping catheter located inside a vascular system of the body of the patient of FIG. 1A, for determining the trajectory which a valve replacement catheter has to follow, from a point of insertion into the vascular system to the malfunctioning valve of the heart, according to an embodiment of the disclosed technique. FIG. 1C is a schematic illustration of an image of the heart of FIG. 1A, illustrating an anatomic position of a malfunctioning heart valve of the heart, marked by a medical staff member on an image of the heart, in accordance with another embodiment of the disclosed technique. FIG. 1D is a schematic illustration of an anatomic position representation of the malfunctioning heart valve of the heart of FIG. 1A, and the current position representation of an artificial heart valve. FIG. 1E is a schematic illustration of the anatomic position representation of the malfunctioning heart valve of the heart of FIG. 1A, and the current position representation of the artificial heart valve of FIG. 1D, when the current position of the artificial heart valve is substantially at the anatomic position of the malfunctioning heart.

With reference to FIG. 1A, heart 100 includes a right ventricle 102, a left ventricle 104, a left atrium 106, a right atrium 108, a tricuspid valve 110, a pulmonary valve 112, an aortic valve 114, and a mitral valve 116. A superior vena cava 118 of the patient opens into right atrium 108. Superior vena cava 118 branches into a left brachiocephalic vein 196, a right brachiocephalic vein 198, and an internal jugular vein 200 of the patient. The description herein below according to one aspect of the disclosed technique, concerns a procedure for fixing an artificial heart valve (not shown) at the position of tricuspid valve 110. It is noted however, that the disclosed technique can be employed for fixing the artificial heart valve, at the position of other valves of heart 100, such as pulmonary valve 112, aortic valve 114, and mitral valve 116.

With reference to FIG. 1B, a medical staff member (not shown) employs a mapping catheter 202, an image acquisition system (not shown), an MPS (not shown), and a processor (not shown), in order to determine a trajectory of a valve replacement catheter 160 (FIG. 1A). Mapping catheter 202 includes an MPS sensor 204 at a distal portion thereof. The MPS is coupled with MPS sensor 204. The processor is coupled with the MPS, the image acquisition system and with a display (not shown).

In the following description, the image acquisition system is a C-arm which acquires a plurality of two-dimensional X-ray images of the vascular system of the patient. Alternatively, the image acquisition system is a computer tomography machine (CT), magnetic resonance imaging machine (MRI), positron emission tomography (PET), single photon emission computer tomography (SPECT), an ultrasound machine, optical coherence tomography (OCT), Intracardiac Echocardiogram (ICE), and the like.

The medical staff member threads mapping catheter 202 to tricuspid valve 110, through left brachiocephalic vein 196 and superior vena cava 118, on a guidewire 168 (FIG. 1A) which was previously threaded through left brachiocephalic vein 196, to tricuspid valve 110. The medical staff member injects a contrast agent into the vascular system of the body of the patient (not shown), and pulls back mapping catheter 202 toward the insertion point. During pullback of mapping catheter 202, the image acquisition system acquires a plurality of two-dimensional images while the contrast agent is active. During the same pullback, the MPS acquires position data respective of the trajectory of mapping catheter 202, in a three-dimensional MPS coordinate system respective of the MPS, corresponding to the respective two-dimensional images, according to an output of MPS sensor 204.

The MPS determines the timing signal of the heart (i.e., ECG) and of the lungs (i.e., the respiration rate) of the patient, according to the output of MPS sensor 204, as described herein below in connection with FIG. 3. Alternatively, the processor is coupled with an ECG monitor (not shown), and with a respiration monitor (not shown). The processor determines the timing signal of the heart and of the lungs, according to output of the ECG monitor and of the respiration monitor.

The processor tags each of the two-dimensional images with the respective position data, and with the timing signal of the heart and of the lungs. The processor produces a three-dimensional topography of the vascular system, along the trajectory of mapping catheter 202, according to the two-dimensional images, the position data, and the timing signals of the heart and of the lungs, by a technique known in the art. The processor can produce the three-dimensional topography by employing a segmentation algorithm known in the art, in order to determine the boundaries of the mapped portion of the vascular system, and to produce a highlighted image thereof.

The image acquisition system can acquire images of the vascular system from different points of view, in order to allow the processor to determine the diameters of the vessels (not shown) at each region, more accurately. Furthermore, the processor can indicate foreshortening effects of the vessels, for example, by employing different colors, or different concentrations of marks (not shown) along the trajectory. Alternatively, the processor can produce the three-dimensional images according to another trajectory of mapping catheter 202, during a forward movement of mapping catheter 202, from the insertion point to the site of tricuspid valve 110, instead of a pullback.

With reference to FIG. 1C, the medical staff member injects the contrast agent a second time, into right ventricle 102 and the image acquisition system acquires a first image (not shown) of heart 100. The medical staff member injects the contrast agent into right atrium 108, and the image acquisition system acquires a second image (not shown) of heart 100. The processor produces a side by side image of the first image and the second image, according to an output of the ECG, such that the first image and the second image are synchronized with the timing signal of heart 100. The display displays the side by side image for the medical staff member. Since the malfunctioning tricuspid valve 110 is generally calcified, the location of tricuspid valve 110 is indicated in gray scale, as a gap (i.e., a septum) between the colored right ventricle 102 and the colored right atrium 108, in the first image and the second image.

The processor, furthermore combines the three-dimensional topography of the vascular system with the side by side image of heart 100. In case the contrast agent remains active from the mapping procedure as described herein above in connection with FIG. 1B, the image acquisition system can produce the side by side image of heart 100 while the contrast agent is still active.

The medical staff member marks the position (i.e., the anatomic position) of tricuspid valve 110, on the side by side image of heart 100 in the three-dimensional MPS coordinate system. This mark is represented by an anatomic heart valve representation 140 in the side by side image of heart 100, on the display. The medical staff member can mark the anatomic position by employing a user interface (not shown), coupled with the processor. The user interface can be a tactile user interface, (e.g., a mouse, tablet and stylus, keyboard, touch-screen), an aural user interface (i.e., a microphone and a loud speaker), a visual user interface (e.g., cathode ray tube display, autostereoscopic display, head-mounted display, volumetric display, multi-LCD (liquid crystal display) display, touch-screen, and the like).

With reference back to FIG. 1A, the medical staff member threads valve replacement catheter 160 along guidewire 168, toward tricuspid valve 110, through left brachiocephalic vein 196, after removing mapping catheter 202 from the vascular system. Alternatively, the medical staff member can insert valve replacement catheter 160 through the inferior vena cava (not shown) of the body of the patient. The medical staff member can maneuver valve replacement catheter 160 through the vascular system either automatically or semi-automatically, by employing a moving mechanism as described herein below, in connection with FIG. 5.

In an automatic mode, the processor controls the operation of a moving mechanism 326 (FIG. 5), to advance valve replacement catheter 160 toward tricuspid valve 110, through the vascular system, according to the three-dimensional topography of the vascular system. Alternatively, the medical staff member can maneuver valve replacement catheter 160 through the vascular system manually, by employing other techniques known in the art.

Valve replacement catheter 160 includes a valve fixation device at a distal portion thereof, for fixing an artificial heart valve at the position of tricuspid valve 110. Valve replacement catheter 160, furthermore includes an MPS sensor 164 at the distal portion thereof, in order to detect the current position of the artificial heart valve. In the example set forth in FIG. 1A, the valve fixation device is in form of an inflatable balloon 162. Inflatable balloon 162 is surrounded by a stent 166 and by the artificial heart valve. However, other valve fixation devices known in the art can be employed in connection with the disclosed technique, such as an elongate tubular manipulator (not shown) which includes an ejector at the tip thereof, for ejecting the artificial heart valve at the position of the tricuspid valve.

With reference to FIG. 1D, the anatomic position of tricuspid valve 110, as marked by the medical staff member according to the description in connection with FIG. 1C herein above, is represented by an anatomic position representation 190. The current position of the tip of valve replacement catheter 160, as detected by MPS sensor 164 (FIG. 1A), is represented by a current position representation 192. In this case, anatomic position representation 190 is in form of a line, and current position representation 192 is in form of a square divided to two rectangles, by a first median line 194.

Both the anatomic position representation 190 and current position representation 192 can be displayed on the display, to enable the medical staff member to monitor the advancement of valve replacement catheter 160 within the vascular system, and within the chambers of heart 100. The processor can combine the three-dimensional topography of the vascular system, the side by side image of heart 100, and a two-dimensional image of heart 100. This two-dimensional image can be a real-time image (e.g., X-ray, ultrasound), a pseudo-real-time cine-loop image of heart 100, and the like.

With reference to FIG. 1E, the processor constantly detects the current position of the tip of valve replacement catheter 160, and thus the current position of the artificial heart valve. When the processor detects that the current position of the artificial heart valve substantially matches the anatomic position of tricuspid valve 110, the processor produces an indication via the user interface or the display. This indication lets the medical staff member know that the artificial heart valve is now positioned at the anatomic position of tricuspid valve 110, and is ready to be fixed in place.

This indication can be a visual indication. When the processor detects that the current position of the artificial heart valve substantially matches the anatomic position of tricuspid valve 110, the processor additionally aligns anatomic position representation 190 with current position representation 192. At this moment, anatomic position representation 190 which is in form of a line, forms the second median line of the square of current position representation 192, thereby forming a new square which includes an image of a cross there within. An image of this new square is displayed on the display, thereby indicating to the medical staff member that the artificial heart valve is now positioned at the anatomic position of tricuspid valve 110, ready to be fixed in place.

Alternatively, this indication can be an aural indication (e.g., in form of a series of acoustical beeps). Further alternatively, this indication can be a haptic indication, by incorporating a tactile user interface, which produces for example, a mechanical vibration.

If the medical staff member activates the valve fixation device and fixes the artificial heart valve in place while the myocardium (i.e., the muscles—not shown) of heart 100 are constantly contracting (i.e., heart 100 is pumping blood in its natural mode), then heart 100 can be irreversibly injured and may even result in sudden death of the patient. The injury to heart 100 can be for example, due to suction of inflatable balloon 162 into right ventricle 102, contact between inflatable balloon 162 and the pacemakers of heart 100, such as Aschoff-Tawara node, Keith-Flack sinus node, the bundle of His, and the like. The suction of inflatable balloon 162 can cause serious injury within the heart chambers of heart 100.

The normal contractions of the myocardium have to be prevented, when valve replacement catheter 160 enters right atrium 108, and during the entire period of fixing the artificial heart valve in place. Normal myocardial contractions can be resumed only after fixing the artificial heart valve in place, after deflating inflatable balloon 162 (i.e., inactivating the valve fixation device), and after pulling back inflatable balloon 162 from the region of tricuspid valve 110. Otherwise, inflatable balloon 162 in its inflated state, can be sucked into right ventricle 102, wherein it is very difficult to evacuate inflatable balloon 162 from right ventricle 102. In this case, the probability of heart failure is quite high.

The medical staff member may induce cardiac arrest in the patient by medical techniques known in the art. The medical staff member can for example, administer a cardioplegic solution to heart 100. In this case, the myocardium ceases to contract substantially completely. In order to administer a cardioplegic solution, a catheter 170 (FIG. 1A) is threaded through the femoral artery (not shown), to an ascending aorta 172 of the patient. Catheter 170 includes a balloon 174 at the tip thereof. Balloon 174 is inflated to occlude the lumen of ascending aorta 172. A cardioplegic solution, such as Potassium Chloride (KCl), is released from the tip of catheter 170, thereby arresting heart 100. Myocardial contractions are resumed after deflating balloon 174, and thus, unblocking ascending aorta 172.

Another technique to prevent the normal contractions of the myocardium is by inducing ventricular fibrillation. Ventricular fibrillation is a cardiac condition in which the ventricular muscles of the heart twitch randomly, rather than contracting in unison, and so the ventricles fail to pump blood into the arteries. Ventricular fibrillation is characterized by oscillations having varying amplitudes, contours, and frequencies. Therefore, inflation of inflatable balloon 162, and the procedure of fixing in place of the artificial heart valve, have substantially no negative influence on heart 100. Ventricular fibrillation can be induced by applying cold packs to the chest (not shown), to reduce the temperature of the myocardium. Once the temperature of the myocardium is raised to the normal level, the myocardial contractions are resumed.

Alternatively, ventricular fibrillation can be induced electrically, by delivering an electric current to the myocardium, via electrodes placed on the exterior surface (not shown) of heart 100. When the flow of electric current to the myocardium is ceased, the myocardial contractions are resumed.

When the medical staff member receives the indication from the user interface that the artificial heart valve is substantially positioned at the position of tricuspid valve 110, she can begin fixing the artificial heart valve in place. At this point, she induces cardiac arrest, according to one of the techniques described herein above. The medical staff member fixes the artificial heart valve at the anatomic position of tricuspid valve 110, by activating the valve fixation device (e.g., by inflating inflatable balloon 162).

During ventricular fibrillation, in which the myocardium flutters in low amplitudes and at high frequencies, the MPS detects the contraction pattern of the myocardium according to an output of MPS sensor 164. In order to prevent injury to heart 100, the medical staff member has to activate the valve fixation device during a relatively dormant phase of the contraction pattern of the myocardium, when the blood flow between right ventricle 102 and right atrium 108 is minimal. The MPS predicts the upcoming contraction pattern of the myocardium, and the user interface produces the respective information, for the medical staff member to activate the valve fixation device during a dormant phase of the contraction pattern, in order to minimize injury to heart 100.

While heart 100 is in a state of cardiac arrest, the medical staff member deflates inflatable balloon 162 (i.e., inactivates the valve fixation device), thereby fixing in place stent 166 together with the artificial heart valve, at the anatomic position of tricuspid valve 110. The medical staff member, then pulls out valve replacement catheter 160 along guidewire 168, such that inflatable balloon 162 leaves the region of tricuspid valve 110. The medical staff member can verify that inflatable balloon 162 is sufficiently far from the region of tricuspid valve 110, for example, by observing the current position representation of MPS sensor 164, superimposed on an image (not shown) of heart 100.

Alternatively, the medical staff member can verify this situation, according to a catheter location gage (not shown), which is incorporated with a control assembly (not shown) of the valve replacement catheter. Once the medical staff member verifies that inflatable balloon 162 is deflated, and is moved out of the region of tricuspid valve 110, she can take the necessary measures in order to resume the normal contractions of the myocardium.

It is noted that by indicating the position of the malfunctioning heart valve, for fixing the artificial heart valve in place, the medical staff member is relieved from the guess work which is usually involved in percutaneous operations. Hence, by employing the method of the disclosed technique, such a medical procedure can be performed at a substantially greater rate of success, involving much less medical risk to the patient.

Alternatively, the MPS determines the respiration activity state, according to a set of MPS sensors (not shown) attached to the body of the patient, as described herein below in connection with the method of FIG. 3. Further alternatively, the processor can determine the respiration activity state according to an output (i.e., respiration timing signal) of a respiration monitor (not shown).

As described herein above, during ventricular fibrillation, the myocardial contractions are in form of irregular undulations of varying amplitudes, contours, and frequencies. Therefore, due to these oscillations, the current true position of tricuspid valve 110 repeatedly varies relative to the coordinates of mark 140 (FIG. 1C), which were stored in the processor during the marking stage by the medical staff member. Hence, the processor has to take into account this discrepancy while determining if the current position of the artificial heart valve substantially matches the anatomic position of tricuspid valve 110 (i.e., if the current position matches the coordinates of mark 140).

For this purpose, the processor constantly corrects the coordinates of mark 140, according to the activity state of heart 100, during ventricular fibrillation. The processor can obtain the activity state of heart 100 from the MPS, which in turn determines the activity state according to the output of MPS sensor 164 (FIG. 1A), as described herein below in connection with FIG. 3. Alternatively, the processor can obtain the activity state from an ECG monitor (not shown) coupled with the body of the patient.

The artificial heart valve constantly moves relative to the anatomic position of tricuspid valve 110, due to the respiratory motion of the lungs of the patient. For this purpose, the processor takes into account the respiratory activity state of the lungs, while it determines if the current position of the artificial heart valve substantially matches the anatomic position of tricuspid valve 110. The processor takes into account the respiratory motion in case the cardiac arrest is induced by either administering the cardioplegic solution or by inducing ventricular fibrillation.

Figure 2:
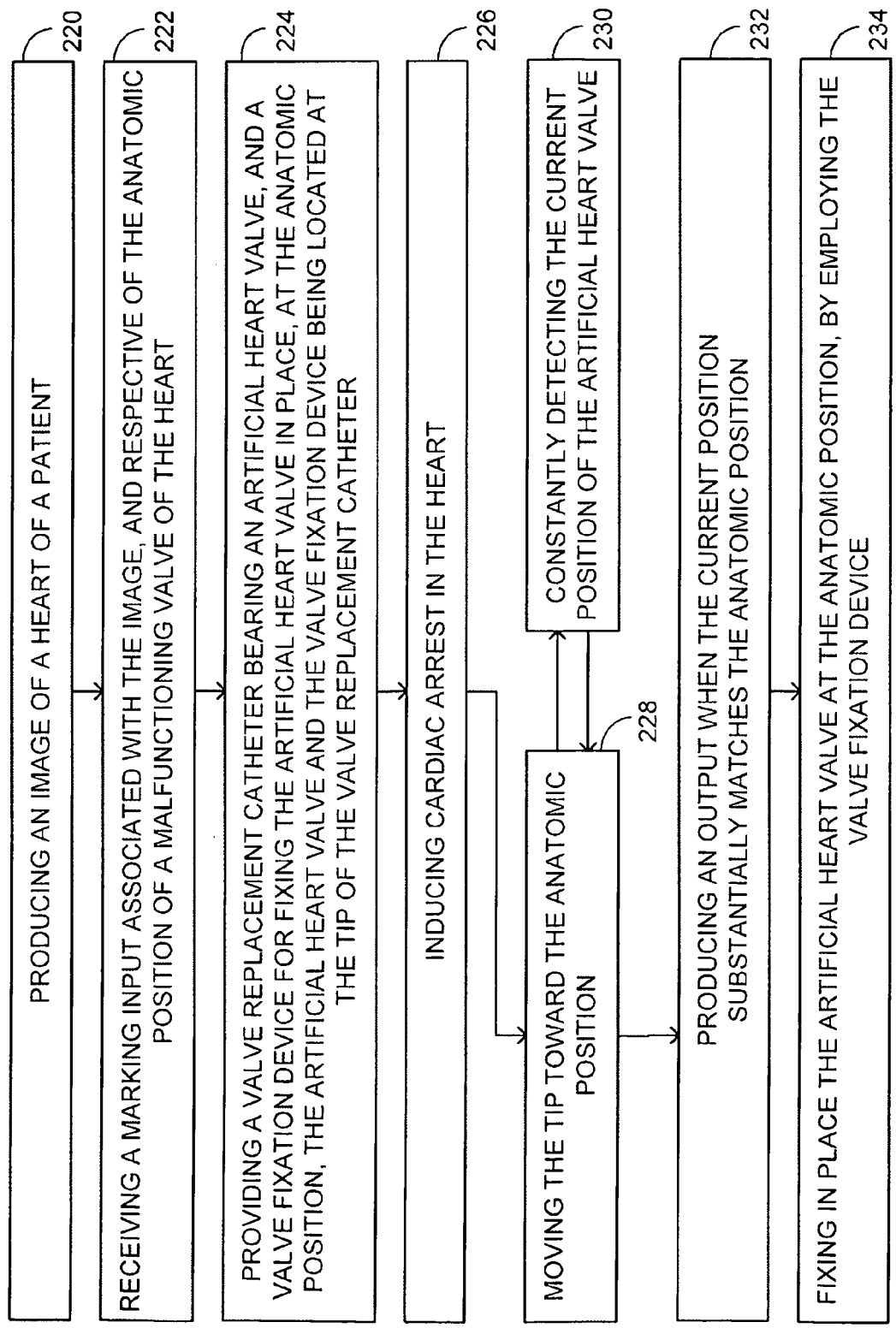
FIG. 2, which is a schematic illustration of a method for performing a percutaneous heart valve replacement operation, operative in accordance with a further embodiment of the disclosed technique.

Reference is now made to FIG. 2, which is a schematic illustration of a method for performing a percutaneous heart valve replacement operation, operative in accordance with a further embodiment of the disclosed technique. In procedure 220, an image of the heart of a patient is produced. The image of the heart can be produced by employing techniques known in the art. This image is a combination of the three-dimensional topography of the vascular system, the side by side image of heart 100, and a two-dimensional image of heart 100 (e.g., a real-time X-ray image).

In procedure 222, a marking input associated with the image, and respective of an anatomic position of a malfunctioning valve of the heart, is received. With reference to FIG. 1C, the medical staff member marks the position of tricuspid valve 110, via the user interface, as anatomic heart valve representation 140, and the processor receives this marking information via the user interface.

In procedure 224, a valve replacement catheter bearing an artificial heart valve and a valve fixation device for fixing in place the artificial heart valve at the anatomic position, is provided, the artificial heart valve and the valve fixation device being located at the tip of the valve replacement catheter. With reference to FIG. 1A, valve replacement catheter 160 is provided to the medical staff member. Valve replacement catheter 160 includes an artificial heart valve and a valve fixation device at the tip thereof.

In procedure 226, cardiac arrest is induced in the heart. With reference to FIG. 1A, when the tip of valve replacement catheter 160 enters right atrium 108 (i.e., a heart chamber of heart 100), cardiac arrest is induced in heart 100.

In procedure 228, the tip is moved toward the anatomic position. The tip can be moved either automatically, semi-automatically, or manually. With reference to FIG. 1A, valve replacement catheter 160 is moved through the vascular system of the patient, toward anatomic position of tricuspid valve 110, while heart 100 is in a state of cardiac arrest.

In procedure 230, the current position of the artificial heart valve is constantly detected. With reference to FIGS. 1A, and 1D, as valve replacement catheter 160 is advancing toward tricuspid valve 110, the MPS detects the current position of the artificial heart valve, according to the output of MPS sensor 164, and the processor receives this position information from the MPS.

In procedure 232, when the current position substantially matches the anatomic position, an indication is produced. With reference to FIG. 1E, when the processor detects that the artificial heart valve is located at the anatomic position of tricuspid valve 110, the processor produces an image of square 192. This image of square 192 includes median lines 190 and 194, and the display displays square 192, thereby letting the medical staff member know that the artificial heart valve is now at the anatomic position, and is ready to be fixed in place. Alternatively, the processor can direct the user interface to produce a series of acoustical beeps.

When the medical staff member verifies that the artificial heart valve is positioned at the anatomic position of tricuspid valve 110, and while heart 100 is in a state of cardiac arrest, the medical staff member fixes the artificial heart valve in place, by activating the valve fixation device (e.g., by inflating inflatable balloon 162—procedure 234).

According to another aspect of the disclosed technique, the following is a description of a method for determining the activity state of an organ, according to MPS data. The term "organ activity state" herein below, refers to either the cardiac activity state of a heart of a patient, or the respiration activity state of the lungs of the patient.

Figure 3:
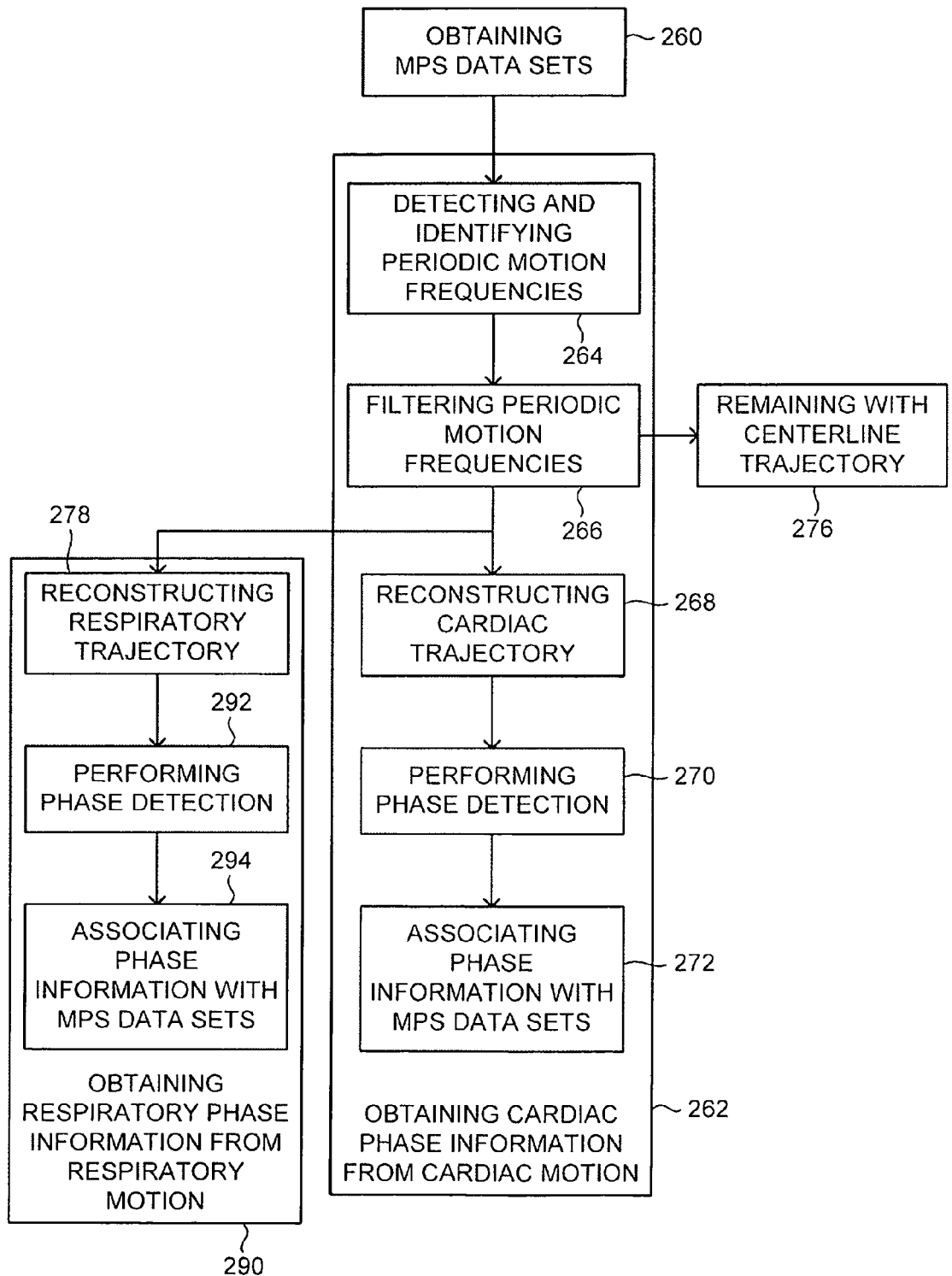
FIG. 3 is a schematic illustration of a method for determining an organ activity state of an heart of a patient, according to position data of an MPS sensor which moves together with the movements of the heart, operative in accordance with another embodiment of the disclosed technique.

Reference is further made to FIG. 3, which is a schematic illustration of a method for determining an organ activity state of an heart of a patient, according to position data of an MPS sensor which moves together with the movements of the heart, operative in accordance with another embodiment of the disclosed technique. In procedure 260, data sets are obtained from an MPS. A two-dimensional image acquisition device is employed for acquiring a series of two-dimensional images of the heart. Each data set includes a series of position coordinate readings of the two-dimensional image acquisition device, the valve replacement catheter, a selected area of the body of the patient, or the operating table on which the patient is lying, respectively, as received from the respective MPS sensor. In the description herein below, reference is made to left brachiocephalic vein 196 (FIG. 1A). However, the description holds true with reference to other veins and arteries which lead to the malfunctioning heart valve of the heart, other than the tricuspid valve.

The MPS processes detected electromagnetic fields to obtain the respective position coordinate readings, which are subsequently stored in a database coupled with the processor. It is recalled that each MPS sensor position coordinate reading is time-tagged, or associated with the exact time at which the reading was obtained. Thus, each MPS data set received from MPS sensor 164 (FIG. 1A), includes a collection of coordinate readings demonstrating the precise motion trajectory of valve replacement catheter 160 over time.

In procedure 262, cardiac phase information is obtained from cardiac motion. In particular, cardiac phase information is obtained from data streams originating from MPS sensor 164 located on valve replacement catheter 160. Procedure 262 consists of procedures 264, 266, 268, 270, and 272.

In procedure 264, periodic motion frequencies are detected and identified in a time-tagged MPS data set. As valve replacement catheter 160 is maneuvered within left brachiocephalic vein 196 (FIG. 1B), the motion of valve replacement catheter 160 is influenced by two additional factors. The first factor relates to the activity of heart 100, or cardiac motion, such as systole and diastole. Cardiac motion affects left brachiocephalic vein 196 in a certain way, such as contraction or expansion in varying degrees and at periodic intervals. The second factor relates to the breathing activity, or respiratory motion, such as inhaling and exhaling. Respiratory motion affects left brachiocephalic vein 196 in a certain way, such as contraction or expansion in varying degrees and at periodic intervals. Taken together, the overall motion of valve replacement catheter 160 is composed of the cardiac motion and the respiratory motion superimposed onto the movement associated with maneuvering valve replacement catheter 160 (which corresponds to the topography of the vascular system).

Since the cardiac motion and respiratory motion are cyclic in nature, the periodic frequencies can be detected in the overall trajectory of valve replacement catheter 160. The specific frequencies relating to the cardiac motion exhibit different characteristics than the specific frequencies relating to the respiratory motion. The specific frequencies relating to the cardiac motion are identified from the detected periodic frequencies. Similarly, the specific frequencies relating to the respiratory motion are identified from the detected periodic frequencies. The processor performs the analysis on the MPS data set and identifies the relevant periodic motion frequencies.

In procedure 266, periodic motion frequencies are filtered from the time-tagged MPS data set. The periodic motion frequencies detected in procedure 264 are separated out from the overall trajectory of valve replacement catheter 160. The remaining motion components correspond to the central axis of the maneuvers of valve replacement catheter 160, which represents the topography of the vascular system, or "centerline trajectory" (referenced procedure 276). The time-tags associated with the MPS data set are retained for each of the filtered periodic motion frequencies. The processor filters out the relevant periodic motion frequencies from the MPS data set.

In procedure 268, the mechanical movement of left brachiocephalic vein 196 due to the cardiac motion, or "cardiac trajectory", is reconstructed from the MPS data sets and from the filtered periodic motion frequencies. In particular, the cardiac trajectory is reconstructed according to the previously identified specific frequencies relating to the cardiac motion. The reconstructed cardiac trajectory may be reflected, for example, by a graph that indicates the trajectory of left brachiocephalic vein 196 due to cardiac motion over a period of time. The processor analyzes the relevant periodic motion frequencies and creates a reconstruction of the cardiac trajectory.

In procedure 278, the mechanical movement of left brachiocephalic vein 196 due to the respiratory motion, or "respiratory trajectory", is reconstructed from the MPS data sets and the filtered periodic motion frequencies. In particular, the respiratory trajectory is reconstructed according to the previously identified specific frequencies relating to the respiratory motion. The reconstructed respiratory trajectory may be reflected, for example, by a graph that indicates the trajectory of left brachiocephalic vein 196 due to respiratory motion over a period of time. The processor analyzes the relevant periodic motion frequencies and creates a reconstruction of the respiratory trajectory.

Reconstruction of the respiratory trajectory may be based solely on coordinate readings obtained from the external reference sensors (i.e., MPS sensors—not shown—attached to the body of the patient and to the operation table—not shown). It is noted that an additional reference sensor (or plurality thereof) may be attached (i.e., externally or internally) to the body of the patient, to monitor breathing patterns, and the like. For example, an intravascular sensor may be used for this purpose.

This sensor functions as a confirmation mechanism to provide supporting data regarding respiratory motion, and more accurately determine periodic motion frequencies relating to respiratory motion. It is noted that the same or an additional sensor (or plurality thereof) may be used for gathering additional cardiac data either as a confirmation mechanism or for providing supporting data for cardiac phase detection.

In procedure 270, phase detection is performed on the reconstructed cardiac trajectory. The cardiac trajectory consists of different phases or activity-states of heart 100, corresponding to different points within a cardiac cycle. The phases repeat themselves periodically with each cycle. The plurality of cardiac activity-states is identified on the reconstructed cardiac trajectory during phase detection. The processor performs the analysis of the cardiac trajectory and identifies the different cardiac cycle phases.

Figure 4A:
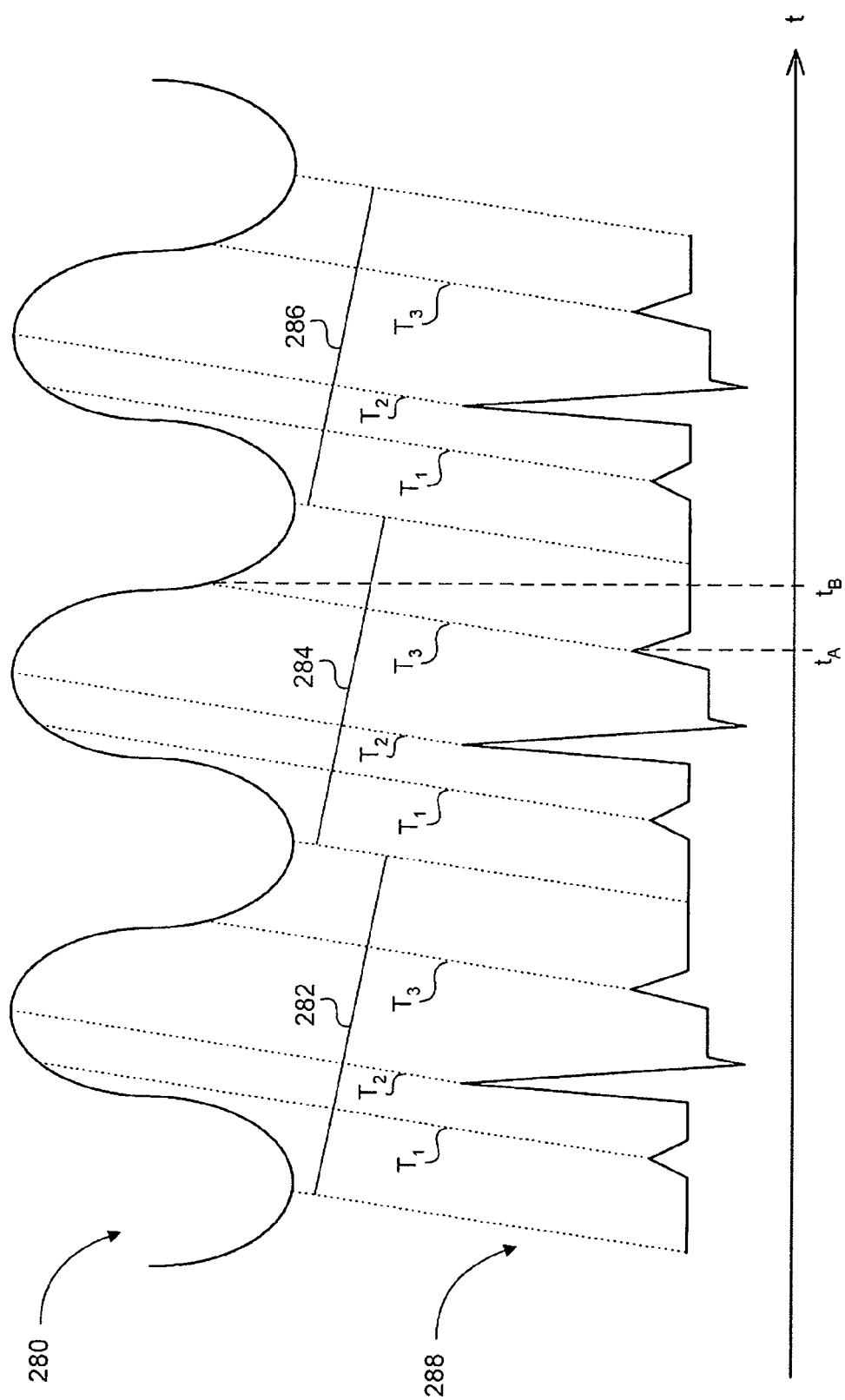
FIG. 4A is a schematic illustration of a cardiac trajectory, in an electrical signal representation and in a mechanical signal representation.

Reference is further made to FIG. 4A, which is a schematic illustration of a cardiac trajectory, in an electrical signal representation and in a mechanical signal representation. The mechanical signal representation of the cardiac trajectory, generally referenced 280, includes a plurality of cardiac activity-states (i.e., cardiac cycle phases), such as activity-states $T_1$, $T_2$ and $T_3$, in each of a plurality of cardiac cycles 282, 284 and 286. The mechanical representation of the cardiac trajectory is equivalent to the cardiac trajectory reconstructed from the MPS data sets and the filtered periodic motion frequencies (procedures 266 and 268). The electrical signal representation of the cardiac trajectory, generally referenced 288, depicts the same activity-states $T_1$, $T_2$ and $T_3$, in each of cardiac cycles 282, 284 and 286.

However, the precise time at which these activity-states occur may be different in the two representations, as there is a slight delay at the electrical representation with respect to the mechanical representation. For example, it is shown that activity-state $T_3$ of cardiac cycle 284 occurs a at time $t_A$ in cardiac trajectory 280 and at a time $t_B$ in cardiac trajectory 288. Therefore, it is necessary to perform an alignment between the activity-states, when using information from the electrical representation for phase detection. The electrical representation 288 of the cardiac trajectory is equivalent to the electrical timing signals obtained by an ECG monitor (not shown).

It is noted that the detection of cardiac phases is performed based solely on data sets originating from at least MPS sensor 164 (FIG. 1A), and perhaps also from the reference sensors attached to the body of the patient and the operation table. These data sets provide a mechanical representation of the cardiac trajectory. No external monitoring device is required to obtain cardiac phase information.

It is noted that phase detection may be performed on the original MPS data sets, rather than on the reconstructed cardiac trajectory, using the detected and filtered periodic motion frequencies. The different phases or activity-states of heart 100 are identified directly on the MPS data sets obtained in procedure 260.

In procedure 272, cardiac phase information is associated with the MPS data sets. Each data set obtained from MPS sensor 164, relating to the position of valve replacement catheter 160 is matched to one of a plurality of activity-states $T_1$, $T_2$ and $T_3$, according to their corresponding time elements (i.e., time-tags). The position of left brachiocephalic vein 196, and consequently the position of valve replacement catheter 160, is different during different activity-states of left brachiocephalic vein 196. The processor associates between a coordinate reading and the matching phase thereof, and stores the information in the database.

Respiratory phase information may be obtained from the respiratory motion, in a similar manner as cardiac phase information is obtained from the cardiac motion. Respiration activity-states may be identified on the reconstructed respiratory trajectory using the periodic motion components relating to the respiratory motion. Respiratory phase information is obtained from respiratory motion in an optional procedure 290. Procedure 290 consists of procedures 278, 292 and 294. In procedure 278, a respiratory trajectory is reconstructed from the MPS data sets and the filtered periodic motion frequencies, as described herein above in connection with procedures 264, 266 and 268.

In procedure 292, phase detection is performed on the reconstructed respiratory trajectory. Like the cardiac trajectory, the respiratory trajectory consists of different phases or activity-states of the lungs (not shown), corresponding to different points within a respiratory cycle. The respiratory activity-states of the lungs can be identified from the phases of the respiratory trajectory. The phases repeat themselves periodically with each cycle. The respiratory activity-states are identified on the reconstructed respiratory trajectory during phase detection. The processor performs the analysis of the respiratory trajectory and identifies the different respiratory cycle phases.

Figure 4B:
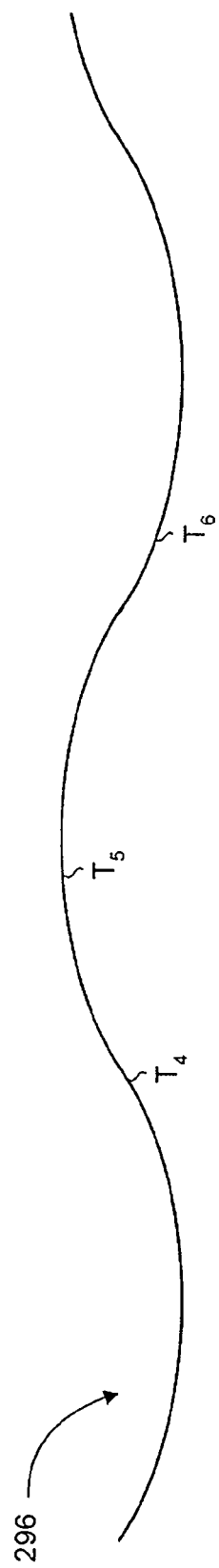
FIG. 4B is a schematic illustration of a respiratory trajectory in a mechanical signal representation.

Reference is further made to FIG. 4B, which is a schematic illustration of a respiratory trajectory in a mechanical signal representation, generally referenced 296. Mechanical signal representation 296 includes a plurality of respiratory activity-states (i.e., respiratory cycle phases), such as activity-states $T_4$, $T_5$ and $T_6$. Mechanical representation 296 is equivalent to the respiratory trajectory reconstructed from the MPS data sets, and the filtered periodic motion frequencies in procedure 268.

It is noted that the detection of respiratory phases is performed based on data sets detected by MPS sensor 164. Alternatively, or in addition, respiratory phase detection may be based on data sets detected by other MPS sensors attached to the body of the patient and to the operation table. These data sets provide a mechanical representation of the respiratory trajectory. No external monitoring device is required to obtain respiratory phase information. It is further noted that phase detection may be performed on the original MPS data sets, rather than on the reconstructed respiratory trajectory, using the detected and filtered periodic motion frequencies. The different phases or activity-states of the lungs are identified directly on the MPS data sets obtained in procedure 260.

It is noted that the actual value of the cardiac rate or respiratory rate of the patient may be obtained without using any external monitoring device (such as an ECG monitor—not shown). The cardiac rate or respiratory rate of the patient can be obtained solely according to the output of the MPS sensors attached to the catheter and the MPS sensors attached to the body of the patient.

In procedure 294, respiratory phase information is associated with the MPS data sets. Each data set obtained from MPS sensor 164, is matched to one of activity-states $T_4$, $T_5$ and $T_6$, according to their corresponding time-tags. Procedure 294 is analogous to procedure 272 discussed herein above.

The term "topological representation" herein below, refers to a mapping of the vascular system which a system according to the disclosed technique employs, in order to maneuver the valve replacement catheter from a point of insertion into the vascular system to the malfunctioning heart valve. The mapping can be either two-dimensional or three-dimensional. Alternatively, it is noted that the term "topological representation" may include just the path to be followed in the vascular system.

Figure 5:
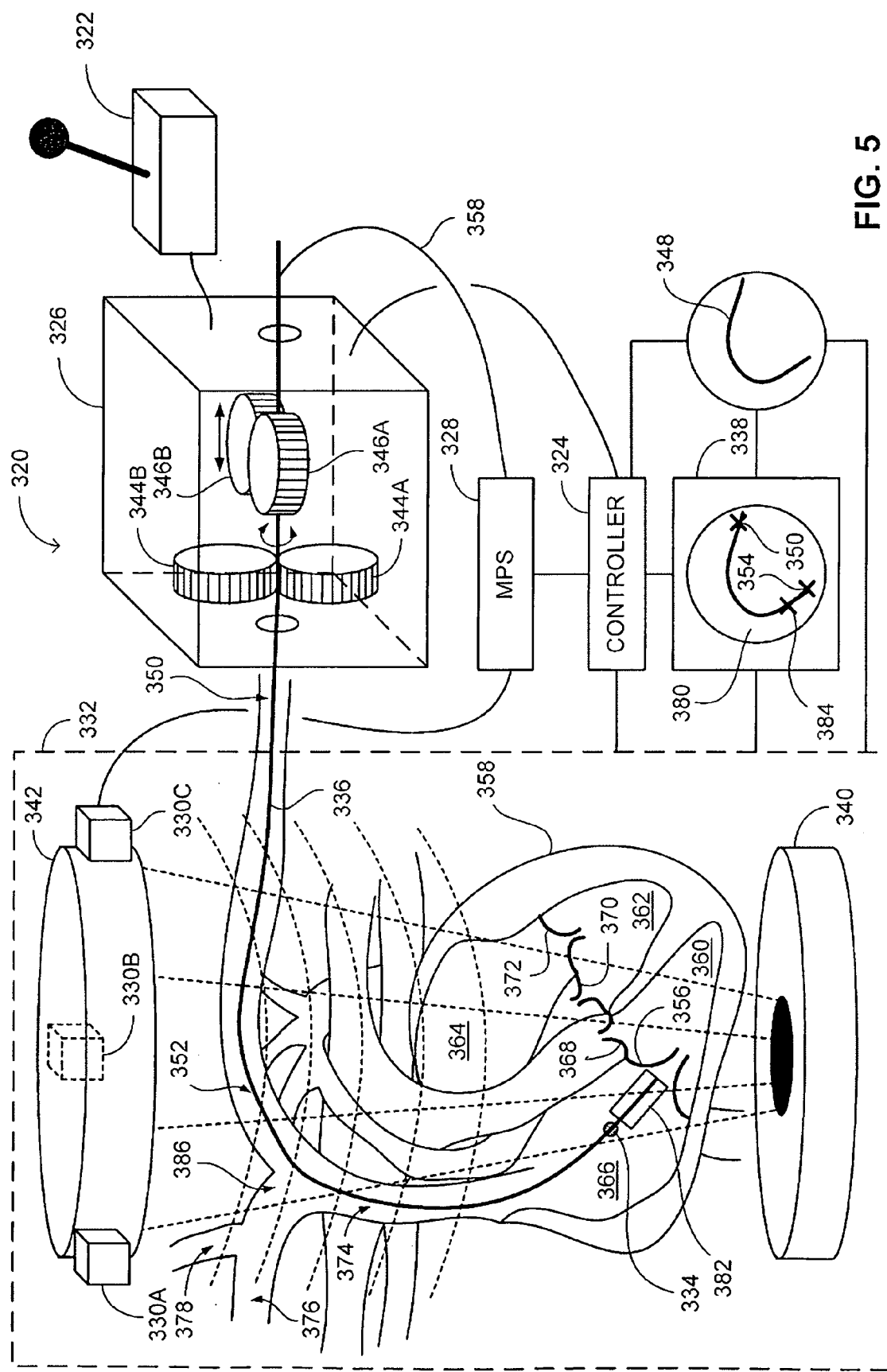
FIG. 5 is a schematic illustration of a system, for automatically maneuvering a valve replacement catheter from a point of insertion into the body of a patient, to a malfunctioning heart valve of the heart of the patient, constructed and operative in accordance with a further embodiment of the disclosed technique.

Reference is further made to FIG. 5, which is a schematic illustration of a system, generally referenced 320, for automatically maneuvering a valve replacement catheter from a point of insertion into the body of a patient, to a malfunctioning heart valve of the heart of the patient, constructed and operative in accordance with a further embodiment of the disclosed technique. System 320 includes a joystick 322, a controller 324, a moving mechanism 326, an MPS 328, a plurality of transmitters 330A, 330B and 330C, an imaging system 332, an MPS sensor 334, a valve replacement catheter 336, and a display 338. Imaging system 332 includes a radiation generator 340 and a radiation detector 342. Imaging system 332 can be an X-ray machine, fluoroscope, C-arm imager, CT, PET, SPECT, ultrasound machine, MRI, and the like. Valve replacement catheter 336 includes a valve fixation device 382 at the tip thereof. A stent (not shown) and an artificial heart valve (not shown) are coupled with valve fixation device 382. MPS sensor 334 is located at the tip of valve replacement catheter 336.

Moving mechanism 326 can include a pair of angular movement rollers 344A and 344B, and a pair of linear movement rollers 346A and 346B, and respective moving elements (not shown) such as electric motors, actuators, and the like. However, moving mechanism 326 can include other, alternative or additional elements, as long as it imparts to valve replacement catheter 336 the necessary motions described herein below (e.g., piezoelectric motors which transfer linear movement through friction). Optionally, moving mechanism 326 can be disposable in order to keep it sterile. Controller 324 includes a processor (not shown) and a storage unit (not shown) for storing information respective of a trajectory 348. According to the description herein below, system 320 enables valve replacement catheter 336 to move within a left brachiocephalic vein 352 within the body of the patient, automatically according to trajectory 348, from a point of entry 350 into left brachiocephalic vein 352, to a destination 354 of a tricuspid valve 356 (i.e., a malfunctioning heart valve) of a heart 358 of the patient.

Heart 358 includes a right ventricle 360, a left ventricle 362, a left atrium 364, a right atrium 366, tricuspid valve 356, a pulmonary valve 368, an aortic valve 370, and a mitral valve 372. A superior vena cava 374 of the patient opens into right atrium 366. Superior vena cava 374 branches into left brachiocephalic vein 352, a right brachiocephalic vein 376, and an internal jugular vein 378 of the patient.

Moving mechanism 326 is coupled with joystick 322 and with controller 324. Controller 324 is coupled with imaging system 332. MPS 328 is coupled with controller 324 and with transmitters 330A, 330B and 330C. MPS sensor 334 is coupled with MPS 328 by a conductor 358 (i.e., a conductive coupling). Display 338 is coupled with MPS 328 and with imaging system 332.

During the percutaneous heart valve replacement operation, the body of the patient including heart 358 and the associated portion of the vascular system, is located between radiation generator 340 and radiation detector 342. Imaging system 332 has at least one degree of freedom, thereby being able to take a plurality of images of the heart 358 and the associated portions of the vascular system, from different directions. Imaging system 332 provides a signal to display 338, respective of a two-dimensional image 380 of the associated portion of the vascular system, for display 338 to display two-dimensional image 380.

Trajectory 348 is a three-dimensional curve between point of entry 350 and destination 354 in the three-dimensional MPS coordinate system. Both point of entry 350 and destination 354 are within a field of view of imaging system 332. Trajectory 348 is determined by employing mapping catheter 202 (FIG. 1B), as described herein above.

The coordinate systems of MPS 328 and imaging system 332 are set to a common two-dimensional coordinate system, for display 338 to superimpose a real-time representation 384 of MPS sensor 334, on two-dimensional image 380, during the movement of valve replacement catheter 336 within left brachiocephalic vein 352. The information displayed by display 338, serves the medical staff member to observe the location of the tip of valve replacement catheter 336, and of the artificial heart valve, during the movement of valve replacement catheter 336 within left brachiocephalic vein 352. This two-dimensional coordinate system can be determined for example, according to the following method.

A first transformation model between the three-dimensional coordinate system of MPS 328 and the three-dimensional coordinate system of imaging system 332 is determined. A second transformation model between the three-dimensional coordinate system of imaging system 332 and a two-dimensional coordinate system of imaging system 332 is determined. The three-dimensional coordinate system of MPS 328 is transformed to the three-dimensional coordinate system of imaging system 332, by applying the first transformation model to the three-dimensional coordinate system of MPS 328. The three-dimensional transformed coordinate system of imaging system 332 is transformed to the two-dimensional coordinate system of imaging system 332, by applying the second transformation model to the three-dimensional transformed coordinate system of imaging system 332.

The first transformation model is determined according to a set of points in the three-dimensional coordinate system of MPS 328 and another set of points in the three-dimensional coordinate system of imaging system 332. The second transformation model is determined according to external parameters of imaging system 332 (i.e., a set of points in the three-dimensional coordinate system of imaging system 332) and internal parameters of imaging system 332 (e.g., lens angle, focal length, magnification).

In response to the electromagnetic field produced by transmitters 330A, 330B and 330C, MPS sensor 334 sends a signal to MPS 328 via conductor 358, respective of the three-dimensional position of MPS sensor 334. Alternatively, MPS sensor 334 is coupled with MPS 328 wirelessly and without conductor 358, in which case MPS sensor 334 sends this position signal to MPS 328 wirelessly.

MPS 328 determines the coordinates of MPS sensor 334 according to the signal received from MPS sensor 334. MPS 328 sends a signal respective of the coordinates of MPS sensor 334 to controller 324, in the three-dimensional coordinate system of MPS 328. MPS 328 sends a signal respective of the coordinates of MPS sensor 334 to display 338, in the two-dimensional coordinate system of imaging system 332, as described herein above.

Throughout the valve replacement operation, display 338 displays two-dimensional image 380 of heart 358 and the associated portion of the vascular system (i.e., a section between point of entry 350 and destination 354) according to a signal received from imaging system 332. Display 338 also displays representation 384 of the current location of MPS sensor 334 (i.e., the distal portion of valve replacement catheter 336), superposed on two-dimensional image 380, according to the signal received from MPS 328. Alternatively, the current position of the MPS sensor can be superposed on a three-dimensional image of the left brachiocephalic vein.

Moving mechanism 326 operates according to the commands received from controller 324, to maneuver valve replacement catheter 336 along trajectory 348, from point of entry 350 to destination 354. For this purpose, the pair of angular movement rollers 344A and 344B twist valve replacement catheter 336 clockwise and counterclockwise relative to the longitudinal axis (not shown) of valve replacement catheter 336, and the pair of linear movement rollers 346A and 346B move valve replacement catheter 336 forward and backward. Controller 324 constantly receives a signal from MPS 328 respective of three-dimensional coordinates of MPS sensor 334 at any given time (i.e., a feedback), thereby allowing moving mechanism 326 to apply corrections to possible errors of movement along trajectory 348. These corrections are applied in the following manner.

Controller 324 sends a signal at predetermined time increments to moving mechanism 326, to advance valve replacement catheter 336 by a predetermined displacement increment. Controller 324 determines the advancement of the tip of valve replacement catheter 336 at each time increment (according to the position signal received from MPS 328), and checks whether this advancement substantially matches the predetermined displacement by which valve replacement catheter 336 was supposed to advance. In case the actual detected advancement does not match the predetermined displacement increment, controller 324 determines that valve replacement catheter 336 has made contact with an obstacle (not shown) which prevents valve replacement catheter 336 to advance according to trajectory 348 (e.g., the tip of valve replacement catheter 336 can be stuck at a bifurcation 386).

In this case, controller 324 sends a signal to moving mechanism 326 to retreat valve replacement catheter 336 by a selected increment backward within the vascular system, and also to twist the distal portion of valve replacement catheter 336 by a selected amount. After this twist, controller 324 sends a signal to moving mechanism 326 to advance valve replacement catheter 336 by a predetermined displacement increment. Thus, moving mechanism 326 can maneuver valve replacement catheter 336 to overcome the obstacle and to enter the predetermined branch (in this case superior vena cava 374 at bifurcation 386).

It is noted that due to the three-dimensional position information which controller 324 receives as a real-time feedback from MPS 328, controller 324 can control the operation of moving mechanism 326 to maneuver valve replacement catheter 336 in three-dimensions. Thus, system 320 provides an advantage over systems in the prior art, in which the medical staff member can maneuver the valve replacement catheter according to a two-dimensional display, only in two dimensions. System 320 provides automatic maneuvering of valve replacement catheter 336 through the vascular system in three dimensions, while performing feedback oriented real time corrections in order to reach destination 354 (i.e., tricuspid valve 356).

It is noted that more than one MPS sensor can be located at the distal portion of the catheter. This arrangement is crucial in case the distal portion of the catheter is provided with a "curve-back" functionality. The "curve-back" movement can be provided for example, by employing Electro Active Polymers (EAP). The moving mechanism is likewise provided with the necessary elements to apply an appropriate torque to the tip of the valve replacement catheter, to bend the tip. Moreover, with the aid of multiple position detectors, the display can display the current geometry of the tip.

Furthermore, the controller can obtain more complete information respective of the geometry of the tip of the valve replacement catheter, when the valve replacement catheter is blocked by an obstacle, and thus expedite the maneuvering operation. For example, if the controller detects that the tip of the valve replacement catheter has unexpectedly bent, then the controller determines that the tip of the valve replacement catheter has made contact with an obstacle in the left brachiocephalic vein. The controller can reach this conclusion for example, by comparing the detected orientation of the MPS sensor at a given point within the left brachiocephalic vein, with the computed slope of the trajectory at the same point within the left brachiocephalic vein. In case the detected orientation and the computed slope do not match, the controller determines that the valve replacement catheter has met an obstacle, thereby directing the moving mechanism to operate in order to move the valve replacement catheter back from the obstacle.

In case the medical staff member is unsatisfied with the automatic operation of moving mechanism 326, she can override controller 324, and manually operate moving mechanism 326 via joystick 322. The medical staff member can intervene in any phase of operation of system 320, using joystick 322. This is a semi-automatic mode of operation of system 320, wherein controller 324 enables moving mechanism 326 to maneuver valve replacement catheter 336 through the trivial portions of trajectory 348, and the medical staff member takes control of system 320 in the more intricate portions of trajectory 348. In case of manual intervention, joystick 322 overcomes any automated action. It is noted that both in the automatic mode and the manual mode, the medical staff member receives a visual feedback of the advancement of valve replacement catheter 336 within left brachiocephalic vein 352, by viewing representation 384 of the tip of valve replacement catheter 336 on display 338.

It will be appreciated by persons skilled in the art that the disclosed technique is not limited to what has been particularly shown and described hereinabove. Rather the scope of the disclosed technique is defined only by the claims, which follow.

The invention claimed is:

1. System for positioning an artificial heart valve at the anatomic position of a malfunctioning heart valve of a heart of a patient, the system comprising:
   a valve fixation device, for fixing said artificial heart valve at said anatomic position;
   a valve replacement catheter, said valve replacement catheter bearing said artificial heart valve and said valve fixation device, at the tip of said valve replacement catheter, said valve replacement catheter being employed for fixing in place said artificial heart valve;
   a first medical positioning system (MPS) sensor located at the tip of said valve replacement catheter;
   an MPS coupled with said first MPS sensor, for determining the current position of said tip of said valve replacement catheter in an MPS coordinate system, according to an output of said first MPS sensor;
   a processor coupled with said MPS, said processor being configured to determine a trajectory along which said valve replacement catheter will move by acquiring position readings of a second MPS sensor disposed in a mapping catheter and coupled to said MPS; and
   a first user interface, coupled with said processor, for receiving a marking input from a user, independent of said trajectory and respective of said anatomic position, said marking input comprising at least position information indicative of said anatomic position and a marking information indicating that the user has affirmatively designated the position information as indicative of said anatomic position;
   said processor determining said anatomic position in said MPS coordinate system, according to said marking input;
   said processor constantly determining said current position, while said valve replacement catheter is moving along said trajectory toward said anatomic position;

said processor producing an indication via said first user interface, when said processor determines that said current position substantially matches said anatomic position.

2. The system according to claim 1, wherein said valve fixation device comprises:
an inflatable balloon; and
a stent surrounding said inflatable balloon, said artificial heart valve being coupled with said stent, and
wherein said artificial heart valve is fixed in place at said anatomic position, by inflating said inflatable balloon.

3. The system according to claim 1, wherein said first user interface is selected from the list consisting of:
tactile user interface;
aural user interface; and
visual user interface.

4. The system according to claim 3, wherein said visual user interface displays an anatomic position representation respective of said anatomic position, and a current position representation respective of said current position.

5. The system according to claim 3, wherein said visual user interface is selected from the list consisting of:
cathode ray tube display;
autostereoscopic display;
head-mounted display;
volumetric display;
multi-liquid-crystal-display; and
touch-screen.

6. The system according to claim 1, further comprising a second user interface coupled with said processor, wherein said processor produces said indication via said second user interface.

7. The system according to claim 6, wherein said second user interface is selected from the list consisting of:
aural;
visual; and
haptic.

8. The system according to claim 1, wherein said malfunctioning heart valve is selected from the list consisting of:
tricuspid valve;
aortic valve;
pulmonary valve; and
mitral valve.

9. The system according to claim 1, wherein said processor determines said trajectory of said mapping catheter from an insertion point into said patient to said anatomic position.

10. The system according to claim 9, wherein said processor constantly determines said current position in relation to said trajectory, while said valve replacement catheter is moving toward said anatomic position.

11. The system according to claim 10, further comprising:
a moving mechanism, coupled with said valve replacement catheter and said processor, for maneuvering said valve replacement catheter in said patient;
wherein said processor operates said moving mechanism;
wherein said processor determines corrections to said current position if said current position in relation to said trajectory does not substantially match a predetermined displacement increment of said valve replacement catheter along said trajectory, and
wherein said moving mechanism applies said corrections to said valve replacement catheter.

* * * * *